United States Patent
Fung et al.

(10) Patent No.: US 9,259,305 B2
(45) Date of Patent: Feb. 16, 2016

(54) GUIDE WIRE LOCKING MECHANISM FOR RAPID EXCHANGE AND OTHER CATHETER SYSTEMS

(75) Inventors: Gregory W. Fung, San Mateo, CA (US); Nianjiong Joan Bei, Foster City, CA (US); Alexander Nikanorov, Palo Alto, CA (US); Danielle D. LaFlash, San Mateo, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 592 days.

(21) Appl. No.: 11/097,010

(22) Filed: Mar. 31, 2005

(65) Prior Publication Data

US 2006/0224176 A1  Oct. 5, 2006

(51) Int. Cl.
| | |
|---|---|
| *A61F 11/00* | (2006.01) |
| *A61F 2/01* | (2006.01) |
| *A61M 25/01* | (2006.01) |
| *A61M 25/09* | (2006.01) |
| *A61M 25/10* | (2013.01) |

(52) U.S. Cl.
CPC .............. *A61F 2/013* (2013.01); *A61M 25/01* (2013.01); *A61M 2025/0183* (2013.01); *A61M 2025/09125* (2013.01); *A61M 2025/1056* (2013.01)

(58) Field of Classification Search
CPC ............. A61F 2/013; A61M 25/01; A61M 2025/1056; A61M 2025/09125; A61M 2025/0183
USPC .......... 600/585; 606/213, 151, 113, 198, 108, 606/200; 604/510
See application file for complete search history.

(56) References Cited

U.S. PATENT DOCUMENTS

| | | | |
|---|---|---|---|
| 3,835,854 A | * | 9/1974 | Jewett ............................. 604/159 |
| 3,952,747 A | | 4/1976 | Kimmell, Jr. |
| 4,425,908 A | | 1/1984 | Simon |
| 4,494,531 A | | 1/1985 | Gianturco |
| 4,612,931 A | | 9/1986 | Dormia |
| 4,619,246 A | | 10/1986 | Molgaard-Nielsen et al. |
| 4,643,184 A | | 2/1987 | Mobin-Uddin |

(Continued)

FOREIGN PATENT DOCUMENTS

| | | |
|---|---|---|
| EP | 0427429 A3 | 9/1991 |
| EP | 0 472 334 A1 | 2/1992 |

(Continued)

OTHER PUBLICATIONS

Dilitation of the Carotid Artery by a Temporary Carotid Filter by A. Beck, St. Milic, A.M. Spagnoli, November-December Issue of OPLITAI, An International Journal on Military Medicine and Health Emergencies, pp. 67-74.

*Primary Examiner* — Rene Towa
(74) *Attorney, Agent, or Firm* — Fulwider Patton LLP

(57) ABSTRACT

A guide wire locking mechanism for a catheter system includes a motion-limiting component adapted to contact a portion of a guide wire and limit the direction of motion that the guide wire can slide therethrough. The motion-limiting component allows the guide wire to slide in one direction when placed in the locking mechanism but prevents the guide wire from moving in the opposite direction. The motion-limiting component can be made from a row of movable teeth having contact surfaces or faces which come in contact with a portion of the guide wire. The teeth are bendable to allow the guide wire to move in one direction but will tighten against the guide wire if one attempts to move the guide wire in an opposite direction.

29 Claims, 3 Drawing Sheets

(56) References Cited

U.S. PATENT DOCUMENTS

| | | | | |
|---|---|---|---|---|
| 4,650,466 | A | 3/1987 | Luther | |
| 4,662,885 | A | 5/1987 | DiPisa, Jr. | |
| 4,688,553 | A | 8/1987 | Metals | |
| 4,706,671 | A | 11/1987 | Weinrib | |
| 4,723,549 | A | 2/1988 | Wholey et al. | |
| 4,727,873 | A | 3/1988 | Mobin-Uddin | |
| 4,781,177 | A | 11/1988 | Lebigot | |
| 4,790,812 | A | 12/1988 | Hawkins, Jr. et al. | |
| 4,790,813 | A | 12/1988 | Kensey | |
| 4,794,928 | A | 1/1989 | Kletschka | |
| 4,832,055 | A | 5/1989 | Palestrant | |
| 4,873,978 | A | 10/1989 | Ginsburg | |
| 4,921,478 | A | 5/1990 | Solano et al. | |
| 4,921,484 | A | 5/1990 | Hillstead | |
| 4,957,117 | A | * 9/1990 | Wysham | 600/585 |
| 4,969,891 | A | 11/1990 | Gewertz | |
| 4,990,156 | A | 2/1991 | Lefebvre | |
| 4,997,435 | A | 3/1991 | Demeter | |
| 4,998,539 | A | 3/1991 | Delsanti | |
| 5,053,008 | A | 10/1991 | Bajaj | |
| 5,064,428 | A | 11/1991 | Cope et al. | |
| 5,071,407 | A | 12/1991 | Termin et al. | |
| 5,092,839 | A | 3/1992 | Kipperman | |
| 5,100,423 | A | 3/1992 | Fearnot | |
| 5,100,425 | A | 3/1992 | Fischell et al. | |
| 5,102,415 | A | 4/1992 | Guenther et al. | |
| 5,108,419 | A | 4/1992 | Reger et al. | |
| 5,131,406 | A | * 7/1992 | Kaltenbach | 600/585 |
| 5,152,777 | A | 10/1992 | Goldberg et al. | |
| 5,158,548 | A | 10/1992 | Lau et al. | |
| 5,160,342 | A | 11/1992 | Reger et al. | |
| 5,190,050 | A | * 3/1993 | Nitzsche | 600/585 |
| 5,192,286 | A | 3/1993 | Phan et al. | |
| 5,324,304 | A | 6/1994 | Rasmussen | |
| 5,329,942 | A | 7/1994 | Gunther et al. | |
| 5,330,482 | A | 7/1994 | Gibbs et al. | |
| 5,346,498 | A | * 9/1994 | Greelis et al. | 606/108 |
| 5,350,398 | A | 9/1994 | Pavcnik et al. | |
| 5,370,657 | A | 12/1994 | Irie | |
| 5,375,612 | A | 12/1994 | Cottenceau et al. | |
| 5,383,887 | A | 1/1995 | Nadal | |
| 5,421,832 | A | 6/1995 | Lefebvre | |
| 5,490,859 | A | 2/1996 | Mische et al. | |
| 5,496,277 | A | 3/1996 | Termin et al. | |
| 5,496,330 | A | 3/1996 | Bates et al. | |
| 5,501,694 | A | 3/1996 | Ressemann et al. | |
| 5,549,626 | A | 8/1996 | Miller et al. | |
| 5,601,568 | A | 2/1997 | Chevillon et al. | |
| 5,601,595 | A | 2/1997 | Smith | |
| 5,626,605 | A | 5/1997 | Irie et al. | |
| 5,634,942 | A | 6/1997 | Chevillon et al. | |
| 5,649,953 | A | 7/1997 | Lefebvre | |
| 5,658,296 | A | 8/1997 | Bates et al. | |
| 5,662,671 | A | 9/1997 | Barbut et al. | |
| 5,669,933 | A | 9/1997 | Simon et al. | |
| 5,681,347 | A | 10/1997 | Cathcart et al. | |
| 5,695,518 | A | 12/1997 | Laerum | |
| 5,695,519 | A | 12/1997 | Summers et al. | |
| 5,720,764 | A | 2/1998 | Naderlinger | |
| 5,725,550 | A | 3/1998 | Nadal | |
| 5,746,767 | A | 5/1998 | Smith | |
| 5,755,790 | A | 5/1998 | Chevillon et al. | |
| 5,769,816 | A | 6/1998 | Barbut et al. | |
| 5,772,674 | A | 6/1998 | Nakhjavan | |
| 5,776,162 | A | 7/1998 | Kleshinski | |
| 5,779,716 | A | 7/1998 | Cano et al. | |
| 5,792,145 | A | 8/1998 | Bates et al. | |
| 5,792,156 | A | 8/1998 | Perouse | |
| 5,792,157 | A | 8/1998 | Mische et al. | |
| 5,795,322 | A | 8/1998 | Boudewijn | |
| 5,800,457 | A | 9/1998 | Gelbfish | |
| 5,800,525 | A | 9/1998 | Bachinski et al. | |
| 5,810,874 | A | 9/1998 | Lefebvre | |
| 5,814,064 | A | 9/1998 | Daniel et al. | |
| 5,827,324 | A | 10/1998 | Cassell et al. | |
| 5,833,650 | A | 11/1998 | Imran | |
| 5,836,868 | A | 11/1998 | Ressemann et al. | |
| 5,846,251 | A | 12/1998 | Hart | |
| 5,846,260 | A | 12/1998 | Maas | |
| 5,848,964 | A | 12/1998 | Samuels | |
| 5,868,708 | A | 2/1999 | Hart et al. | |
| 5,868,755 | A | 2/1999 | Kanner et al. | |
| 5,876,367 | A | 3/1999 | Kaganov et al. | |
| 5,897,567 | A | 4/1999 | Ressemann et al. | |
| 5,910,154 | A | 6/1999 | Tsugita et al. | |
| 5,911,734 | A | 6/1999 | Tsugita et al. | |
| 5,935,139 | A | 8/1999 | Bates | |
| 5,941,869 | A | 8/1999 | Patterson et al. | |
| 5,941,896 | A | 8/1999 | Kerr | |
| 5,944,728 | A | 8/1999 | Bates | |
| 5,954,745 | A | 9/1999 | Gertler et al. | |
| 5,968,071 | A | 10/1999 | Chevillon et al. | |
| 5,976,172 | A | 11/1999 | Homsma et al. | |
| 5,980,555 | A | 11/1999 | Barbut et al. | |
| 5,989,281 | A | 11/1999 | Barbut et al. | |
| 6,001,118 | A | 12/1999 | Daniel et al. | |
| 6,007,557 | A | 12/1999 | Ambrisco et al. | |
| 6,013,093 | A | 1/2000 | Nott et al. | |
| 6,022,336 | A | 2/2000 | Zadno-Azizi et al. | |
| 6,027,520 | A | 2/2000 | Tsugita et al. | |
| 6,042,598 | A | 3/2000 | Tsugita et al. | |
| 6,051,015 | A | 4/2000 | Maahs | |
| 6,053,932 | A | 4/2000 | Daniel et al. | |
| 6,059,814 | A | 5/2000 | Ladd | |
| 6,066,158 | A | 5/2000 | Engelson et al. | |
| 6,074,357 | A | 6/2000 | Kaganov et al. | |
| 6,086,605 | A | 7/2000 | Barbut et al. | |
| 6,090,097 | A | 7/2000 | Barbut et al. | |
| 6,096,053 | A | 8/2000 | Bates | |
| 6,099,534 | A | 8/2000 | Bates et al. | |
| 6,099,549 | A | 8/2000 | Bosma et al. | |
| 6,117,154 | A | 9/2000 | Barbut et al. | |
| 6,129,739 | A | 10/2000 | Khosravi | |
| 6,136,015 | A | 10/2000 | Kurz | |
| 6,136,016 | A | 10/2000 | Barbut et al. | |
| 6,142,987 | A | 11/2000 | Tsugita | |
| 6,152,946 | A | 11/2000 | Broome et al. | |
| 6,152,947 | A | 11/2000 | Ambrisco et al. | |
| 6,165,198 | A | 12/2000 | McGurk et al. | |
| 6,165,200 | A | 12/2000 | Tsugita et al. | |
| 6,168,579 | B1 | 1/2001 | Tsugita et al. | |
| 6,168,604 | B1 | 1/2001 | Cano | |
| 6,171,234 | B1 | * 1/2001 | White et al. | 600/102 |
| 6,171,327 | B1 | 1/2001 | Daniel et al. | |
| 6,171,328 | B1 | 1/2001 | Addis | |
| 6,174,318 | B1 | 1/2001 | Bates et al. | |
| 6,176,849 | B1 | 1/2001 | Yang et al. | |
| 6,179,859 | B1 | 1/2001 | Bates et al. | |
| 6,179,860 | B1 | 1/2001 | Fulton, III et al. | |
| 6,179,861 | B1 | 1/2001 | Khosravi et al. | |
| 6,187,025 | B1 | 2/2001 | Machek | |
| 6,203,561 | B1 | 3/2001 | Ramee et al. | |
| 6,206,868 | B1 | 3/2001 | Parodi | |
| 6,214,026 | B1 | 4/2001 | Lepak et al. | |
| 6,224,620 | B1 | 5/2001 | Maahs | |
| 6,235,044 | B1 | 5/2001 | Root et al. | |
| 6,235,045 | B1 | 5/2001 | Barbut et al. | |
| 6,238,412 | B1 | 5/2001 | Dubrul et al. | |
| 6,241,746 | B1 | 6/2001 | Bosma et al. | |
| 6,245,012 | B1 | 6/2001 | Kleshinski | |
| 6,245,087 | B1 | 6/2001 | Addis | |
| 6,245,088 | B1 | 6/2001 | Lowery | |
| 6,245,089 | B1 | 6/2001 | Daniel et al. | |
| 6,251,122 | B1 | 6/2001 | Tsukernik | |
| 6,254,633 | B1 | 7/2001 | Pinchuk et al. | |
| 6,258,115 | B1 | 7/2001 | Dubrul | |
| 6,258,120 | B1 | 7/2001 | McKenzie et al. | |
| 6,264,663 | B1 | 7/2001 | Cano | |
| 6,264,672 | B1 | 7/2001 | Fisher | |
| 6,267,776 | B1 | 7/2001 | O'Connell | |
| 6,267,777 | B1 | 7/2001 | Bosma et al. | |
| 6,270,477 | B1 | 8/2001 | Bagaoisan | |
| 6,270,513 | B1 | 8/2001 | Tsugita et al. | |
| 6,273,901 | B1 | 8/2001 | Whitcher et al. | |

(56) References Cited

U.S. PATENT DOCUMENTS

| | | |
|---|---|---|
| 6,277,138 B1 | 8/2001 | Levinson et al. |
| 6,277,139 B1 | 8/2001 | Levinson et al. |
| 6,280,451 B1 | 8/2001 | Bates et al. |
| 6,287,321 B1 | 9/2001 | Jang |
| 6,290,656 B1 | 9/2001 | Boyle et al. |
| 6,290,710 B1 | 9/2001 | Cryer et al. |
| 6,295,989 B1 | 10/2001 | Connors, III |
| 6,306,163 B1 | 10/2001 | Fitz |
| 6,319,242 B1 | 11/2001 | Patterson et al. |
| 6,319,268 B1 | 11/2001 | Ambrisco et al. |
| 6,325,815 B1 | 12/2001 | Kusleika et al. |
| 6,336,934 B1 | 1/2002 | Gilson et al. |
| 6,340,364 B2 | 1/2002 | Kanesaka |
| 6,340,465 B1 | 1/2002 | Hsu et al. |
| 6,346,116 B1 | 2/2002 | Brooks et al. |
| 6,348,056 B1 | 2/2002 | Bates et al. |
| 6,355,051 B1 | 3/2002 | Sisskind et al. |
| 6,358,199 B1 * | 3/2002 | Pauker et al. ................ 600/114 |
| 6,361,545 B1 | 3/2002 | Macoviak et al. |
| 6,361,546 B1 | 3/2002 | Khosravi |
| 6,364,895 B1 | 4/2002 | Greenhalgh |
| 6,364,896 B1 | 4/2002 | Addis |
| 6,371,969 B1 | 4/2002 | Tsugita et al. |
| 6,371,970 B1 | 4/2002 | Khosravi et al. |
| 6,371,971 B1 | 4/2002 | Tsugita et al. |
| 6,375,670 B1 | 4/2002 | Greenhalgh |
| 6,383,206 B1 | 5/2002 | Gillick et al. |
| 6,384,062 B1 | 5/2002 | Ikeda et al. |
| 6,391,044 B1 | 5/2002 | Yadav et al. |
| 6,394,978 B1 | 5/2002 | Boyle et al. |
| 6,395,014 B1 | 5/2002 | Macoviak et al. |
| 6,398,756 B2 | 6/2002 | Peterson et al. |
| 6,402,771 B1 | 6/2002 | Palmer et al. |
| 6,406,471 B1 | 6/2002 | Jang et al. |
| 6,423,032 B2 | 7/2002 | Parodi |
| 6,423,086 B1 | 7/2002 | Barbut et al. |
| 6,425,909 B1 | 7/2002 | Dieck et al. |
| 6,428,559 B1 | 8/2002 | Johnson |
| 6,432,122 B1 | 8/2002 | Gilson et al. |
| 6,436,121 B1 | 8/2002 | Blom |
| 6,443,926 B1 | 9/2002 | Kletschka |
| 6,443,971 B1 | 9/2002 | Boylan et al. |
| 6,443,972 B1 | 9/2002 | Bosma |
| 6,443,979 B1 | 9/2002 | Stalker et al. |
| 6,447,530 B1 | 9/2002 | Ostrovsky et al. |
| 6,447,531 B1 | 9/2002 | Amplatz |
| 6,450,989 B2 | 9/2002 | Dubrul et al. |
| 6,458,139 B1 | 10/2002 | Palmer et al. |
| 6,461,370 B1 | 10/2002 | Gray et al. |
| 6,468,291 B2 | 10/2002 | Bates et al. |
| 6,482,222 B1 | 11/2002 | Bruckheimer et al. |
| 6,485,456 B1 | 11/2002 | Kletschka |
| 6,485,497 B2 | 11/2002 | Wensel et al. |
| 6,485,500 B1 | 11/2002 | Kokish et al. |
| 6,485,501 B1 | 11/2002 | Green |
| 6,485,502 B2 | 11/2002 | Don Michael et al. |
| 6,485,507 B1 | 11/2002 | Walak et al. |
| 6,494,895 B2 | 12/2002 | Addis |
| 6,499,487 B1 | 12/2002 | McKenzie et al. |
| 6,500,166 B1 | 12/2002 | Zadno Azizi et al. |
| 6,506,203 B1 | 1/2003 | Boyle et al. |
| 6,506,205 B2 | 1/2003 | Goldberg et al. |
| 6,511,492 B1 | 1/2003 | Rosenbluth et al. |
| 6,511,496 B1 | 1/2003 | Huter et al. |
| 6,511,497 B1 | 1/2003 | Braun et al. |
| 6,511,503 B1 | 1/2003 | Burkett et al. |
| 6,514,273 B1 | 2/2003 | Voss et al. |
| 6,517,550 B1 | 2/2003 | Konya et al. |
| 6,517,559 B1 | 2/2003 | O'Connell |
| 6,520,978 B1 | 2/2003 | Blackledge et al. |
| 6,527,746 B1 | 3/2003 | Oslund et al. |
| 6,527,791 B2 | 3/2003 | Fisher |
| 6,530,939 B1 | 3/2003 | Hopkins et al. |
| 6,530,940 B2 | 3/2003 | Fisher |
| 6,533,800 B1 | 3/2003 | Barbut |
| 6,537,294 B1 | 3/2003 | Boyle et al. |
| 6,537,295 B2 | 3/2003 | Petersen |
| 6,537,296 B2 | 3/2003 | Levinson et al. |
| 6,537,297 B2 | 3/2003 | Tsugita et al. |
| 6,540,722 B1 | 4/2003 | Boyle et al. |
| 6,540,767 B1 | 4/2003 | Walak et al. |
| 6,540,768 B1 | 4/2003 | Diaz et al. |
| 6,544,276 B1 | 4/2003 | Azizi |
| 6,544,279 B1 | 4/2003 | Hopkins et al. |
| 6,544,280 B1 | 4/2003 | Daniel et al. |
| 6,547,759 B1 | 4/2003 | Fisher |
| 6,551,268 B1 | 4/2003 | Kaganov et al. |
| 6,551,341 B2 | 4/2003 | Boylan et al. |
| 6,551,342 B1 | 4/2003 | Shen et al. |
| 6,558,401 B1 | 5/2003 | Azizi |
| 6,558,405 B1 | 5/2003 | McInnes |
| 6,562,058 B2 | 5/2003 | Seguin |
| 6,565,591 B2 | 5/2003 | Kelly et al. |
| 6,569,184 B2 | 5/2003 | Huter |
| 6,575,995 B1 | 6/2003 | Huter et al. |
| 6,575,996 B1 | 6/2003 | Denison et al. |
| 6,575,997 B1 | 6/2003 | Palmer et al. |
| 6,582,447 B1 | 6/2003 | Patel et al. |
| 6,582,448 B1 | 6/2003 | Boyle et al. |
| 6,585,756 B1 | 7/2003 | Strecker |
| 6,589,263 B1 | 7/2003 | Hopkins et al. |
| 6,589,265 B1 | 7/2003 | Palmer et al. |
| 6,592,546 B1 | 7/2003 | Barbut et al. |
| 6,592,606 B2 | 7/2003 | Huter et al. |
| 6,592,607 B1 | 7/2003 | Palmer et al. |
| 6,592,616 B1 | 7/2003 | Stack et al. |
| 6,596,011 B2 | 7/2003 | Johnson et al. |
| 6,599,307 B1 | 7/2003 | Huter et al. |
| 6,599,308 B2 | 7/2003 | Amplatz |
| 6,602,269 B2 | 8/2003 | Wallace et al. |
| 6,602,271 B2 | 8/2003 | Adams et al. |
| 6,602,272 B2 | 8/2003 | Boylan et al. |
| 6,602,273 B2 | 8/2003 | Marshall |
| 6,605,102 B1 | 8/2003 | Mazzocchi et al. |
| 6,605,111 B2 | 8/2003 | Bose et al. |
| 6,607,506 B2 | 8/2003 | Kletschka |
| 6,610,077 B1 | 8/2003 | Hancock et al. |
| 6,616,679 B1 | 9/2003 | Khosravi et al. |
| 6,616,680 B1 | 9/2003 | Thielen |
| 6,616,681 B2 | 9/2003 | Hanson et al. |
| 6,616,682 B2 | 9/2003 | Joergensen et al. |
| 6,620,148 B1 | 9/2003 | Tsugita et al. |
| 6,620,182 B1 | 9/2003 | Khosravi |
| 6,623,450 B1 | 9/2003 | Dutta |
| 6,629,953 B1 | 10/2003 | Boyd |
| 6,632,236 B2 | 10/2003 | Hogendijk |
| 6,632,241 B1 | 10/2003 | Hancock et al. |
| 6,635,068 B1 | 10/2003 | Dubrul et al. |
| 6,635,070 B2 | 10/2003 | Leeflang et al. |
| 6,638,293 B1 | 10/2003 | Makowner et al. |
| 6,638,294 B1 | 10/2003 | Palmer |
| 6,645,220 B1 | 11/2003 | Huter et al. |
| 6,645,221 B1 | 11/2003 | Richter |
| 6,645,223 B2 | 11/2003 | Boyle et al. |
| 6,645,224 B2 | 11/2003 | Gilson et al. |
| 6,652,480 B1 | 11/2003 | Imran et al. |
| 6,652,505 B1 | 11/2003 | Tsugita et al. |
| 6,652,554 B1 | 11/2003 | Wholey et al. |
| 6,652,557 B1 | 11/2003 | MacDonald |
| 6,656,202 B2 | 12/2003 | Papp et al. |
| 6,656,203 B2 | 12/2003 | Roth et al. |
| 6,656,204 B2 | 12/2003 | Ambrisco et al. |
| 6,656,351 B2 | 12/2003 | Boyle |
| 6,660,021 B1 | 12/2003 | Palmer et al. |
| 6,663,650 B2 | 12/2003 | Sepetka et al. |
| 6,663,651 B2 | 12/2003 | Krolik et al. |
| 6,663,652 B2 | 12/2003 | Daniel et al. |
| 6,673,090 B2 | 1/2004 | Root et al. |
| 6,676,666 B2 | 1/2004 | Vrba et al. |
| 6,676,682 B1 | 1/2004 | Tsugita et al. |
| 6,676,683 B1 | 1/2004 | Addis |
| 6,679,902 B1 | 1/2004 | Boyle et al. |
| 6,679,903 B2 | 1/2004 | Kurz |
| 6,682,546 B2 | 1/2004 | Amplatz |

(56) References Cited

U.S. PATENT DOCUMENTS

| | | |
|---|---|---|
| 6,685,722 B1 | 2/2004 | Rosenbluth et al. |
| 6,689,151 B2 | 2/2004 | Becker et al. |
| 6,692,513 B2 | 2/2004 | Streeter et al. |
| 6,695,813 B1 | 2/2004 | Boyle et al. |
| 6,695,858 B1 | 2/2004 | Dubrul et al. |
| 6,695,864 B2 | 2/2004 | Macoviak et al. |
| 6,696,666 B2 | 2/2004 | Merdan et al. |
| 6,699,260 B2 | 3/2004 | Dubrul et al. |
| 6,702,834 B1 | 3/2004 | Boylan et al. |
| 6,706,055 B2 | 3/2004 | Douk et al. |
| 6,712,834 B2 | 3/2004 | Yassour et al. |
| 6,712,835 B2 | 3/2004 | Mazzocchi et al. |
| 6,716,231 B1 | 4/2004 | Rafiee et al. |
| 6,723,085 B2 | 4/2004 | Jang et al. |
| 6,726,701 B2 | 4/2004 | Gilson |
| 6,726,702 B2 | 4/2004 | Khosravi |
| 6,726,703 B2 | 4/2004 | Broome et al. |
| 6,740,061 B1 | 5/2004 | Oslund et al. |
| 6,743,247 B1 | 6/2004 | Levinson et al. |
| 6,746,469 B2 | 6/2004 | Mouw |
| 6,752,819 B1 | 6/2004 | Brady et al. |
| 6,755,846 B1 | 6/2004 | Yadav |
| 6,758,855 B2 | 7/2004 | Fulton, III et al. |
| 6,761,727 B1 | 7/2004 | Ladd |
| 6,773,448 B2 | 8/2004 | Kusleika et al. |
| 6,790,219 B1 | 9/2004 | Murphy |
| 6,793,666 B2 | 9/2004 | Hansen et al. |
| 6,793,668 B1 | 9/2004 | Fisher |
| 6,800,080 B1 | 10/2004 | Bates |
| 6,814,739 B2 | 11/2004 | Secrest et al. |
| 6,818,006 B2 | 11/2004 | Douk et al. |
| 6,837,898 B2 | 1/2005 | Boyle |
| 6,840,950 B2 | 1/2005 | Stanford et al. |
| 6,843,798 B2 | 1/2005 | Kusleika et al. |
| 6,846,316 B2 | 1/2005 | Abrams |
| 6,846,317 B1 | 1/2005 | Nigon |
| 6,863,696 B2 | 3/2005 | Kantsevitcha et al. |
| 6,866,677 B2 | 3/2005 | Douk et al. |
| 6,872,216 B2 | 3/2005 | Daniel et al. |
| 6,878,151 B2 | 4/2005 | Carrison et al. |
| 6,878,153 B2 | 4/2005 | Linder et al. |
| 6,887,256 B2 | 5/2005 | Gilson et al. |
| 6,887,257 B2 | 5/2005 | Salahieh et al. |
| 6,887,258 B2 | 5/2005 | Denison |
| 6,888,098 B1 | 5/2005 | Merdan et al. |
| 6,890,340 B2 | 5/2005 | Duane |
| 6,890,341 B2 | 5/2005 | Dieck et al. |
| 6,893,450 B2 | 5/2005 | Foster |
| 6,893,451 B2 | 5/2005 | Cano et al. |
| 6,896,690 B1 | 5/2005 | Lambrecht et al. |
| 6,896,691 B2 | 5/2005 | Boylan |
| 6,902,540 B2 | 6/2005 | Dorros et al. |
| 6,908,474 B2 | 6/2005 | Hogendijk et al. |
| 6,911,036 B2 | 6/2005 | Douk et al. |
| 6,913,612 B2 | 7/2005 | Palmer et al. |
| 6,918,921 B2 | 7/2005 | Brady et al. |
| 6,929,652 B1 | 8/2005 | Andrews |
| 6,932,830 B2 | 8/2005 | Ungs |
| 6,932,831 B2 | 8/2005 | Forber |
| 6,936,058 B2 | 8/2005 | Forde et al. |
| 6,936,059 B2 | 8/2005 | Belef |
| 6,939,361 B1 | 9/2005 | Kleshinski |
| 6,939,362 B2 | 9/2005 | Boyle et al. |
| 6,942,673 B2 | 9/2005 | Bates et al. |
| 6,949,103 B2 | 9/2005 | Mazzocchi et al. |
| 6,951,570 B2 | 10/2005 | Linder et al. |
| 6,953,471 B1 | 10/2005 | Lilly et al. |
| 6,953,472 B2 | 10/2005 | Palmer et al. |
| 6,958,074 B2 | 10/2005 | Russell |
| 6,960,370 B2 | 11/2005 | Monni et al. |
| 6,962,598 B2 | 11/2005 | Linder et al. |
| 6,964,670 B1 | 11/2005 | Shah |
| 6,964,672 B2 | 11/2005 | Brady |
| 6,964,673 B2 | 11/2005 | Tsugita et al. |
| 6,969,395 B2 | 11/2005 | Eskuri |
| 6,969,396 B2 | 11/2005 | Krolik et al. |
| 6,969,397 B2 * | 11/2005 | Ginn .................. 606/213 |
| 6,969,402 B2 | 11/2005 | Bales et al. |
| 6,970,730 B2 | 11/2005 | Fuimaono et al. |
| 6,972,025 B2 | 12/2005 | WasDyke |
| 6,973,340 B2 | 12/2005 | Fuimaono et al. |
| 6,974,468 B2 | 12/2005 | DoBrava et al. |
| 6,974,469 B2 | 12/2005 | Broome et al. |
| 6,979,343 B2 | 12/2005 | Russo et al. |
| 6,979,344 B2 | 12/2005 | Jones et al. |
| 6,986,778 B2 | 1/2006 | Zadno-Azizi |
| 6,989,019 B2 | 1/2006 | Mazzocchi |
| 6,989,021 B2 | 1/2006 | Bosma et al. |
| 6,989,027 B2 | 1/2006 | Allen et al. |
| 6,991,641 B2 | 1/2006 | Diaz et al. |
| 6,991,642 B2 | 1/2006 | Petersen |
| RE38,972 E | 2/2006 | Purdy |
| 6,994,718 B2 | 2/2006 | Groothuis et al. |
| 6,997,938 B2 | 2/2006 | Wang et al. |
| 6,997,939 B2 | 2/2006 | Linder et al. |
| 7,001,406 B2 | 2/2006 | Eskuri et al. |
| 7,001,407 B2 | 2/2006 | Hansen et al. |
| 7,004,954 B1 | 2/2006 | Voss et al. |
| 7,004,955 B2 | 2/2006 | Shen et al. |
| 7,004,956 B2 | 2/2006 | Palmer et al. |
| 7,004,964 B2 | 2/2006 | Thompson et al. |
| 7,011,671 B2 | 3/2006 | Welch |
| 7,011,672 B2 | 3/2006 | Barbut et al. |
| 7,014,647 B2 | 3/2006 | Brady et al. |
| 7,018,372 B2 | 3/2006 | Casey |
| 7,018,385 B2 | 3/2006 | Bates et al. |
| 7,018,393 B1 | 3/2006 | Boyle et al. |
| 7,029,440 B2 | 4/2006 | Broome et al. |
| 7,033,375 B2 | 4/2006 | Mazzocchi et al. |
| 7,037,320 B2 | 5/2006 | Brady et al. |
| 7,041,116 B2 | 5/2006 | Goto et al. |
| 7,044,958 B2 | 5/2006 | Douk et al. |
| 7,048,752 B2 | 5/2006 | Mazzocchi |
| 7,048,758 B2 | 5/2006 | Boyle et al. |
| 7,056,328 B2 | 6/2006 | Arnott |
| 7,060,082 B2 | 6/2006 | Goll et al. |
| 7,077,854 B2 | 7/2006 | Khosravi |
| 7,094,243 B2 | 8/2006 | Mulholland |
| 7,094,249 B1 | 8/2006 | Broome et al. |
| 7,097,440 B2 | 8/2006 | Papp et al. |
| 7,097,651 B2 | 8/2006 | Harrison et al. |
| 7,101,379 B2 | 9/2006 | Gregory, Jr et al. |
| 7,101,380 B2 | 9/2006 | Khachin et al. |
| 7,108,707 B2 | 9/2006 | Huter et al. |
| 2002/0042626 A1 * | 4/2002 | Hanson et al. .................. 606/200 |
| 2002/0091408 A1 | 7/2002 | Sutton et al. |
| 2002/0091409 A1 | 7/2002 | Sutton et al. |
| 2002/0095141 A1 | 7/2002 | Belef et al. |
| 2002/0099407 A1 | 7/2002 | Becker et al. |
| 2002/0103501 A1 | 8/2002 | Diaz et al. |
| 2002/0107541 A1 | 8/2002 | Vale et al. |
| 2002/0111648 A1 | 8/2002 | Kusleika et al. |
| 2002/0111649 A1 | 8/2002 | Russo et al. |
| 2002/0115942 A1 | 8/2002 | Stanford et al. |
| 2002/0120286 A1 | 8/2002 | Dobrava et al. |
| 2002/0120287 A1 | 8/2002 | Huter |
| 2002/0121472 A1 | 9/2002 | Garner et al. |
| 2002/0123720 A1 | 9/2002 | Kusleika et al. |
| 2002/0123755 A1 | 9/2002 | Lowe et al. |
| 2002/0128679 A1 | 9/2002 | Turovskiy et al. |
| 2002/0128680 A1 | 9/2002 | Pavlovic |
| 2002/0128681 A1 | 9/2002 | Broome et al. |
| 2002/0133092 A1 | 9/2002 | Oslund et al. |
| 2002/0138094 A1 | 9/2002 | Borillo et al. |
| 2002/0138095 A1 | 9/2002 | Mazzocchi et al. |
| 2002/0143360 A1 | 10/2002 | Douk et al. |
| 2002/0143361 A1 | 10/2002 | Douk et al. |
| 2002/0151927 A1 | 10/2002 | Douk et al. |
| 2002/0156456 A1 | 10/2002 | Fisher |
| 2002/0156457 A1 | 10/2002 | Fisher |
| 2002/0161390 A1 | 10/2002 | Mouw |
| 2002/0161392 A1 | 10/2002 | Dubrul |
| 2002/0161393 A1 | 10/2002 | Demond et al. |
| 2002/0161395 A1 | 10/2002 | Douk et al. |

(56) References Cited

U.S. PATENT DOCUMENTS

| | | |
|---|---|---|
| 2002/0165576 A1 | 11/2002 | Boyle et al. |
| 2002/0169414 A1 | 11/2002 | Kletschka |
| 2002/0169458 A1 | 11/2002 | Connors, III |
| 2002/0169472 A1 | 11/2002 | Douk et al. |
| 2002/0169474 A1 | 11/2002 | Kusleika et al. |
| 2002/0173815 A1 | 11/2002 | Hogendijk et al. |
| 2002/0173817 A1 | 11/2002 | Kletschka et al. |
| 2002/0177789 A1* | 11/2002 | Ferry et al. ............... 600/585 |
| 2002/0188313 A1 | 12/2002 | Johnson et al. |
| 2002/0188314 A1 | 12/2002 | Anderson et al. |
| 2002/0193825 A1 | 12/2002 | McGuckin et al. |
| 2002/0193826 A1 | 12/2002 | McGuckin et al. |
| 2002/0193827 A1 | 12/2002 | McGuckin et al. |
| 2002/0193828 A1 | 12/2002 | Griffin et al. |
| 2003/0004536 A1 | 1/2003 | Boylan et al. |
| 2003/0004537 A1* | 1/2003 | Boyle et al. ............... 606/200 |
| 2003/0004539 A1 | 1/2003 | Linder et al. |
| 2003/0004540 A1 | 1/2003 | Linder et al. |
| 2003/0004541 A1 | 1/2003 | Linder et al. |
| 2003/0009188 A1 | 1/2003 | Linder et al. |
| 2003/0009189 A1 | 1/2003 | Gilson et al. |
| 2003/0015206 A1 | 1/2003 | Roth et al. |
| 2003/0018354 A1 | 1/2003 | Roth et al. |
| 2003/0023265 A1 | 1/2003 | Forber |
| 2003/0028238 A1 | 2/2003 | Burkett et al. |
| 2003/0032941 A1 | 2/2003 | Boyle et al. |
| 2003/0032977 A1 | 2/2003 | Brady |
| 2003/0040772 A1 | 2/2003 | Hyodoh et al. |
| 2003/0042186 A1 | 3/2003 | Boyle et al. |
| 2003/0045898 A1 | 3/2003 | Harrison et al. |
| 2003/0057156 A1 | 3/2003 | Peterson et al. |
| 2003/0060782 A1 | 3/2003 | Bose et al. |
| 2003/0060843 A1 | 3/2003 | Boucher |
| 2003/0060844 A1 | 3/2003 | Borillo et al. |
| 2003/0065354 A1 | 4/2003 | Boyle et al. |
| 2003/0069596 A1 | 4/2003 | Eskuri |
| 2003/0069597 A1 | 4/2003 | Petersen |
| 2003/0078519 A1 | 4/2003 | Salahieh et al. |
| 2003/0078614 A1 | 4/2003 | Salahieh et al. |
| 2003/0083692 A1 | 5/2003 | Vrba et al. |
| 2003/0083693 A1 | 5/2003 | Daniel et al. |
| 2003/0100917 A1 | 5/2003 | Boyle et al. |
| 2003/0100918 A1 | 5/2003 | Duane |
| 2003/0105484 A1 | 6/2003 | Boyle et al. |
| 2003/0109824 A1 | 6/2003 | Anderson et al. |
| 2003/0114879 A1 | 6/2003 | Euteneuer et al. |
| 2003/0114880 A1 | 6/2003 | Hansen et al. |
| 2003/0120303 A1 | 6/2003 | Boyle et al. |
| 2003/0130680 A1 | 7/2003 | Russell |
| 2003/0130681 A1 | 7/2003 | Ungs |
| 2003/0130682 A1 | 7/2003 | Broome et al. |
| 2003/0130684 A1 | 7/2003 | Brady et al. |
| 2003/0130685 A1 | 7/2003 | Daniel et al. |
| 2003/0130686 A1 | 7/2003 | Daniel et al. |
| 2003/0130687 A1 | 7/2003 | Daniel et al. |
| 2003/0130688 A1 | 7/2003 | Daniel et al. |
| 2003/0135162 A1 | 7/2003 | Deyette, Jr. et al. |
| 2003/0135232 A1 | 7/2003 | Douk et al. |
| 2003/0139764 A1 | 7/2003 | Levinson et al. |
| 2003/0144685 A1 | 7/2003 | Boyle et al. |
| 2003/0144689 A1 | 7/2003 | Brady et al. |
| 2003/0150821 A1 | 8/2003 | Bates et al. |
| 2003/0153935 A1 | 8/2003 | Mialhe |
| 2003/0153941 A1 | 8/2003 | Rourke |
| 2003/0153942 A1 | 8/2003 | Wang et al. |
| 2003/0153943 A1 | 8/2003 | Michael et al. |
| 2003/0158574 A1 | 8/2003 | Esch et al. |
| 2003/0163064 A1 | 8/2003 | Vrba et al. |
| 2003/0171771 A1 | 9/2003 | Anderson et al. |
| 2003/0171803 A1 | 9/2003 | Shimon |
| 2003/0176884 A1 | 9/2003 | Berrada et al. |
| 2003/0176885 A1 | 9/2003 | Broome et al. |
| 2003/0176886 A1 | 9/2003 | Wholey et al. |
| 2003/0176889 A1 | 9/2003 | Boyle et al. |
| 2003/0176909 A1 | 9/2003 | Kusleika et al. |
| 2003/0181942 A1 | 9/2003 | Sutton et al. |
| 2003/0181943 A1 | 9/2003 | Daniel et al. |
| 2003/0187474 A1 | 10/2003 | Keegan et al. |
| 2003/0187475 A1 | 10/2003 | Tsugita et al. |
| 2003/0187495 A1 | 10/2003 | Cully et al. |
| 2003/0191493 A1 | 10/2003 | Epstein et al. |
| 2003/0195554 A1 | 10/2003 | Shen et al. |
| 2003/0195555 A1 | 10/2003 | Khairkhahan et al. |
| 2003/0195556 A1 | 10/2003 | Stack et al. |
| 2003/0199819 A1 | 10/2003 | Beck |
| 2003/0199921 A1 | 10/2003 | Palmer et al. |
| 2003/0204168 A1 | 10/2003 | Bosme et al. |
| 2003/0204202 A1 | 10/2003 | Palmer et al. |
| 2003/0208222 A1 | 11/2003 | Zadno-Azizi |
| 2003/0208224 A1 | 11/2003 | Broome |
| 2003/0208225 A1 | 11/2003 | Goll et al. |
| 2003/0208226 A1 | 11/2003 | Bruckheimer et al. |
| 2003/0208227 A1 | 11/2003 | Thomas |
| 2003/0208228 A1 | 11/2003 | Gilson et al. |
| 2003/0208229 A1 | 11/2003 | Kletschka |
| 2003/0212361 A1 | 11/2003 | Boyle et al. |
| 2003/0212429 A1 | 11/2003 | Keegan et al. |
| 2003/0212431 A1 | 11/2003 | Brady et al. |
| 2003/0212434 A1 | 11/2003 | Thielen |
| 2003/0216774 A1 | 11/2003 | Larson |
| 2003/0220665 A1 | 11/2003 | Eskuri et al. |
| 2003/0225418 A1 | 12/2003 | Eskuri et al. |
| 2003/0225435 A1 | 12/2003 | Huter et al. |
| 2003/0229295 A1 | 12/2003 | Houde et al. |
| 2003/0229374 A1 | 12/2003 | Brady et al. |
| 2003/0233117 A1 | 12/2003 | Adams et al. |
| 2003/0236545 A1 | 12/2003 | Gilson |
| 2004/0002730 A1 | 1/2004 | Denison et al. |
| 2004/0006361 A1 | 1/2004 | Boyle et al. |
| 2004/0006364 A1 | 1/2004 | Ladd |
| 2004/0006365 A1 | 1/2004 | Brady et al. |
| 2004/0006366 A1 | 1/2004 | Huter et al. |
| 2004/0006367 A1 | 1/2004 | Johnson et al. |
| 2004/0006368 A1 | 1/2004 | Mazzocchi et al. |
| 2004/0015184 A1 | 1/2004 | Boyle et al. |
| 2004/0019363 A1 | 1/2004 | Hanson et al. |
| 2004/0034385 A1 | 2/2004 | Gilson et al. |
| 2004/0039411 A1 | 2/2004 | Gilson et al. |
| 2004/0044359 A1 | 3/2004 | Renati et al. |
| 2004/0044360 A1 | 3/2004 | Lowe |
| 2004/0049226 A1 | 3/2004 | Keegan et al. |
| 2004/0059372 A1 | 3/2004 | Tsugita |
| 2004/0059373 A1 | 3/2004 | Shapiro et al. |
| 2004/0082697 A1 | 4/2004 | R tzsch et al. |
| 2004/0082968 A1 | 4/2004 | Krolik et al. |
| 2004/0088000 A1 | 5/2004 | Muller |
| 2004/0088002 A1 | 5/2004 | Boyle et al. |
| 2004/0093009 A1 | 5/2004 | Denison et al. |
| 2004/0093010 A1 | 5/2004 | Gesswein et al. |
| 2004/0093011 A1 | 5/2004 | Vrba |
| 2004/0093012 A1 | 5/2004 | Cully et al. |
| 2004/0093013 A1 | 5/2004 | Brady et al. |
| 2004/0098022 A1 | 5/2004 | Barone |
| 2004/0098026 A1 | 5/2004 | Joergensen et al. |
| 2004/0098032 A1 | 5/2004 | Papp et al. |
| 2004/0098033 A1 | 5/2004 | Leeflang et al. |
| 2004/0102806 A1 | 5/2004 | Broome et al. |
| 2004/0102807 A1 | 5/2004 | Kusleika et al. |
| 2004/0106944 A1 | 6/2004 | Daniel et al. |
| 2004/0111111 A1 | 6/2004 | Lin |
| 2004/0116960 A1 | 6/2004 | Demond et al. |
| 2004/0122466 A1 | 6/2004 | Bales |
| 2004/0127933 A1 | 7/2004 | Demond et al. |
| 2004/0127934 A1 | 7/2004 | Gilson et al. |
| 2004/0127936 A1 | 7/2004 | Salahieh et al. |
| 2004/0138693 A1 | 7/2004 | Eskuri et al. |
| 2004/0138694 A1 | 7/2004 | Tran et al. |
| 2004/0138696 A1 | 7/2004 | Drasler et al. |
| 2004/0147955 A1 | 7/2004 | Beulke et al. |
| 2004/0153118 A1 | 8/2004 | Clubb et al. |
| 2004/0153119 A1 | 8/2004 | Kusleika et al. |
| 2004/0158275 A1 | 8/2004 | Crank et al. |
| 2004/0158277 A1 | 8/2004 | Lowe et al. |
| 2004/0158278 A1 | 8/2004 | Becker et al. |

(56) References Cited

U.S. PATENT DOCUMENTS

| | | |
|---|---|---|
| 2004/0158279 A1 | 8/2004 | Petersen |
| 2004/0158280 A1 | 8/2004 | Morris et al. |
| 2004/0158281 A1 | 8/2004 | Boylan et al. |
| 2004/0167564 A1 | 8/2004 | Fedie |
| 2004/0167565 A1 | 8/2004 | Beulke et al. |
| 2004/0167566 A1 | 8/2004 | Beulke et al. |
| 2004/0167567 A1 | 8/2004 | Cano et al. |
| 2004/0167568 A1 | 8/2004 | Boyle et al. |
| 2004/0172055 A1 | 9/2004 | Huter et al. |
| 2004/0176794 A1 | 9/2004 | Khosravi |
| 2004/0193208 A1 | 9/2004 | Talpade et al. |
| 2004/0199198 A1 | 10/2004 | Beulke et al. |
| 2004/0199199 A1 | 10/2004 | Krolik et al. |
| 2004/0199203 A1 | 10/2004 | Oslund et al. |
| 2004/0204737 A1 | 10/2004 | Boismier et al. |
| 2004/0210250 A1 | 10/2004 | Eskuri |
| 2004/0220608 A1 | 11/2004 | D'Aquanni et al. |
| 2004/0220609 A1 | 11/2004 | Douk et al. |
| 2004/0220611 A1 | 11/2004 | Ogle |
| 2004/0225321 A1 | 11/2004 | Krolik et al. |
| 2004/0225322 A1 | 11/2004 | Garrison et al. |
| 2004/0236368 A1 | 11/2004 | McGuckin, Jr. et al. |
| 2004/0236369 A1 | 11/2004 | Dubrul |
| 2004/0249409 A1 | 12/2004 | Krolik et al. |
| 2004/0254601 A1 | 12/2004 | Eskuri |
| 2004/0254602 A1 | 12/2004 | Lehe et al. |
| 2004/0260308 A1 | 12/2004 | Gilson et al. |
| 2004/0260333 A1 | 12/2004 | Dubrul et al. |
| 2004/0267301 A1 | 12/2004 | Boylan et al. |
| 2004/0267302 A1 | 12/2004 | Gilson et al. |
| 2005/0004594 A1 | 1/2005 | Nool et al. |
| 2005/0004595 A1 | 1/2005 | Boyle et al. |
| 2005/0004597 A1 | 1/2005 | McGuckin, Jr. et al. |
| 2005/0010245 A1 | 1/2005 | Wasicek |
| 2005/0010246 A1 | 1/2005 | Streeter et al. |
| 2005/0010247 A1 | 1/2005 | Kusleika et al. |
| 2005/0021075 A1 | 1/2005 | Bonnette et al. |
| 2005/0021076 A1 | 1/2005 | Mazzocchi et al. |
| 2005/0055048 A1 | 3/2005 | Dieck et al. |
| 2005/0070953 A1 | 3/2005 | Riley |
| 2005/0075663 A1 | 4/2005 | Boyle et al. |
| 2005/0080446 A1 | 4/2005 | Gilson et al. |
| 2005/0085842 A1 | 4/2005 | Eversull et al. |
| 2005/0090845 A1 | 4/2005 | Boyd |
| 2005/0090857 A1 | 4/2005 | Kusleika et al. |
| 2005/0090858 A1 | 4/2005 | Pavlovic |
| 2005/0096691 A1 | 5/2005 | Groothuis et al. |
| 2005/0096692 A1 | 5/2005 | Linder et al. |
| 2005/0101986 A1 | 5/2005 | Daniel et al. |
| 2005/0101987 A1 | 5/2005 | Salahieh |
| 2005/0101988 A1 | 5/2005 | Stanford et al. |
| 2005/0101989 A1 | 5/2005 | Cully et al. |
| 2005/0113865 A1 | 5/2005 | Daniel et al. |
| 2005/0119688 A1 | 6/2005 | Bergheim |
| 2005/0119689 A1 | 6/2005 | Mazzocchi et al. |
| 2005/0119690 A1 | 6/2005 | Mazzocchi et al. |
| 2005/0119691 A1 | 6/2005 | Daniel et al. |
| 2005/0124931 A1 | 6/2005 | Fulton et al. |
| 2005/0125023 A1 | 6/2005 | Bates et al. |
| 2005/0131450 A1 | 6/2005 | Nicholson et al. |
| 2005/0131453 A1 | 6/2005 | Parodi |
| 2005/0149110 A1 | 7/2005 | Wholey et al. |
| 2005/0149112 A1 | 7/2005 | Barbut |
| 2005/0149113 A1 | 7/2005 | Douk et al. |
| 2005/0159772 A1 | 7/2005 | Lowe et al. |
| 2005/0159773 A1 | 7/2005 | Broome et al. |
| 2005/0159774 A1 | 7/2005 | Belef |
| 2005/0171573 A1 | 8/2005 | Salahieh et al. |
| 2005/0177187 A1 | 8/2005 | Gray et al. |
| 2005/0182330 A1* | 8/2005 | Brockway et al. ............ 600/486 |
| 2005/0182440 A1 | 8/2005 | Bates et al. |
| 2005/0182441 A1 | 8/2005 | Denison et al. |
| 2005/0192623 A1 | 9/2005 | Mazzocchi et al. |
| 2005/0192624 A1 | 9/2005 | Mazzocchi et al. |
| 2005/0203567 A1 | 9/2005 | Linder et al. |
| 2005/0203568 A1 | 9/2005 | Burg et al. |
| 2005/0203569 A1 | 9/2005 | Kusleika et al. |
| 2005/0203570 A1 | 9/2005 | Mazzocchi et al. |
| 2005/0203571 A1 | 9/2005 | Mazzocchi et al. |
| 2005/0209634 A1 | 9/2005 | Brady et al. |
| 2005/0209635 A1 | 9/2005 | Gilson et al. |
| 2005/0216051 A1 | 9/2005 | Mazzocchi et al. |
| 2005/0216052 A1 | 9/2005 | Mazzocchi et al. |
| 2005/0216053 A1 | 9/2005 | Douk et al. |
| 2005/0222583 A1 | 10/2005 | Cano et al. |
| 2005/0222604 A1 | 10/2005 | Schaeffer |
| 2005/0222607 A1 | 10/2005 | Palmer et al. |
| 2005/0228437 A1 | 10/2005 | Gilson et al. |
| 2005/0228438 A1 | 10/2005 | Sachar et al. |
| 2005/0228439 A1 | 10/2005 | Andrews et al. |
| 2005/0234502 A1 | 10/2005 | Gilson et al. |
| 2005/0240215 A1 | 10/2005 | Ellis |
| 2005/0245866 A1 | 11/2005 | Azizi |
| 2005/0267517 A1 | 12/2005 | Ungs |
| 2005/0283184 A1 | 12/2005 | Gilson et al. |
| 2005/0283185 A1 | 12/2005 | Linder et al. |
| 2005/0283186 A1 | 12/2005 | Berrada et al. |
| 2005/0288705 A1 | 12/2005 | Gilson et al. |
| 2006/0004403 A1 | 1/2006 | Gilson et al. |
| 2006/0004405 A1 | 1/2006 | Salahieh et al. |
| 2006/0015138 A1 | 1/2006 | Gertner et al. |
| 2006/0015139 A1 | 1/2006 | Tsugita et al. |
| 2006/0015140 A1 | 1/2006 | Tsugita et al. |
| 2006/0015141 A1 | 1/2006 | Linder et al. |
| 2006/0020285 A1 | 1/2006 | Niermann |
| 2006/0020286 A1 | 1/2006 | Niermann |
| 2006/0025803 A1 | 2/2006 | Mitelberg et al. |
| 2006/0025804 A1 | 2/2006 | Krolik et al. |
| 2006/0025805 A1 | 2/2006 | DoBrava et al. |
| 2006/0030876 A1 | 2/2006 | Peacock, III et al. |
| 2006/0030877 A1 | 2/2006 | Martinez et al. |
| 2006/0030878 A1 | 2/2006 | Anderson et al. |
| 2006/0052817 A1 | 3/2006 | Russo et al. |
| 2006/0074446 A1 | 4/2006 | Gilson et al. |
| 2006/0095069 A1 | 5/2006 | Shah et al. |
| 2006/0100659 A1 | 5/2006 | Dinh et al. |
| 2006/0100662 A1 | 5/2006 | Daniel et al. |
| 2006/0100663 A1 | 5/2006 | Palmer et al. |
| 2006/0116715 A1 | 6/2006 | Khosravi et al. |
| 2006/0122643 A1 | 6/2006 | Wasicek |
| 2006/0122644 A1 | 6/2006 | Brady et al. |
| 2006/0122645 A1 | 6/2006 | Brady et al. |
| 2006/0129181 A1 | 6/2006 | Callol et al. |
| 2006/0129182 A1 | 6/2006 | Gilson et al. |
| 2006/0129183 A1 | 6/2006 | Boyle et al. |
| 2006/0149312 A1 | 7/2006 | Arguello et al. |
| 2006/0149313 A1 | 7/2006 | Arguello et al. |
| 2006/0149314 A1 | 7/2006 | Borillo et al. |
| 2006/0155322 A1 | 7/2006 | Sater et al. |
| 2006/0161198 A1 | 7/2006 | Sakai et al. |
| 2006/0167491 A1 | 7/2006 | Wholey et al. |
| 2006/0184194 A1 | 8/2006 | Pal et al. |
| 2006/0190025 A1 | 8/2006 | Lehe et al. |
| 2006/0195137 A1 | 8/2006 | Sepetka et al. |
| 2006/0195138 A1 | 8/2006 | Goll et al. |
| 2006/0200047 A1 | 9/2006 | Galdonik et al. |
| 2006/0200191 A1 | 9/2006 | Zadno-Azizi |
| 2006/0206139 A1 | 9/2006 | Tekulve |

FOREIGN PATENT DOCUMENTS

| | | |
|---|---|---|
| EP | 0533511 A1 | 3/1993 |
| FR | 2580504 A1 | 10/1986 |
| GB | 2020557 | 11/1979 |
| WO | WO92/03097 | 3/1992 |
| WO | WO96/01591 | 1/1996 |
| WO | WO97/17100 | 5/1997 |
| WO | WO98/02084 | 1/1998 |
| WO | WO98/33443 | 8/1998 |
| WO | WO99/23976 | 5/1999 |
| WO | WO99/44510 | 9/1999 |
| WO | WO00/67667 | 11/2000 |

(56) References Cited

FOREIGN PATENT DOCUMENTS

| WO | WO01/10346 | 2/2001 | | |
| WO | WO01/45592 | 6/2001 | | |
| WO | WO01/87183 | 11/2001 | | |
| WO | WO 02/069844 | 9/2002 | | |
| WO | WO 03/086209 | 10/2003 | | |
| WO | WO 2004071352 A1 * | 8/2004 | ................ | A61F 2/06 |

* cited by examiner

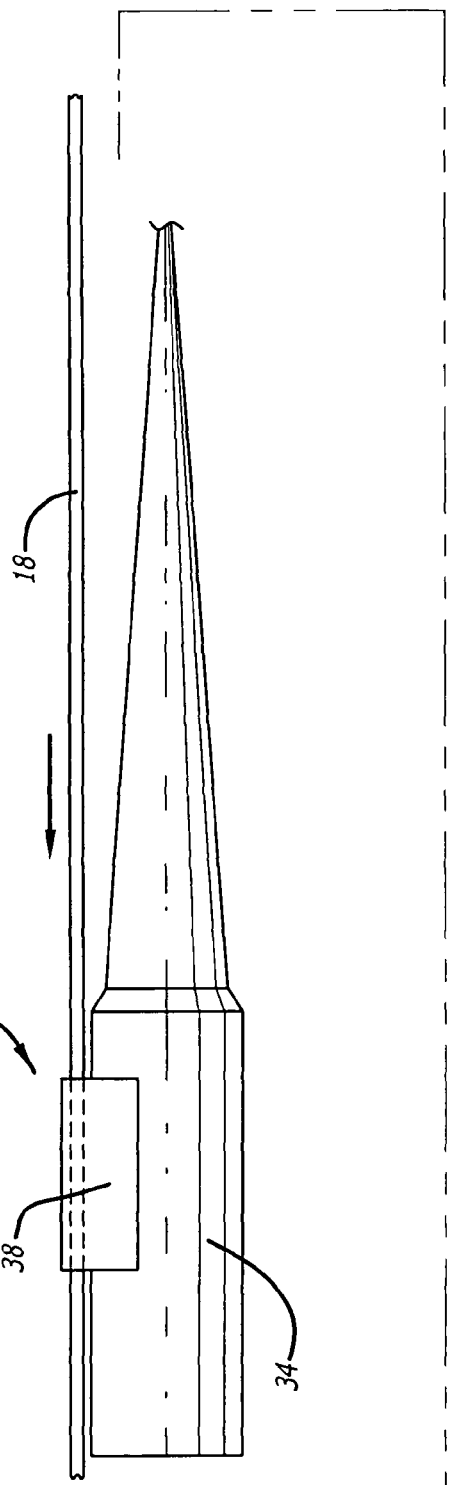
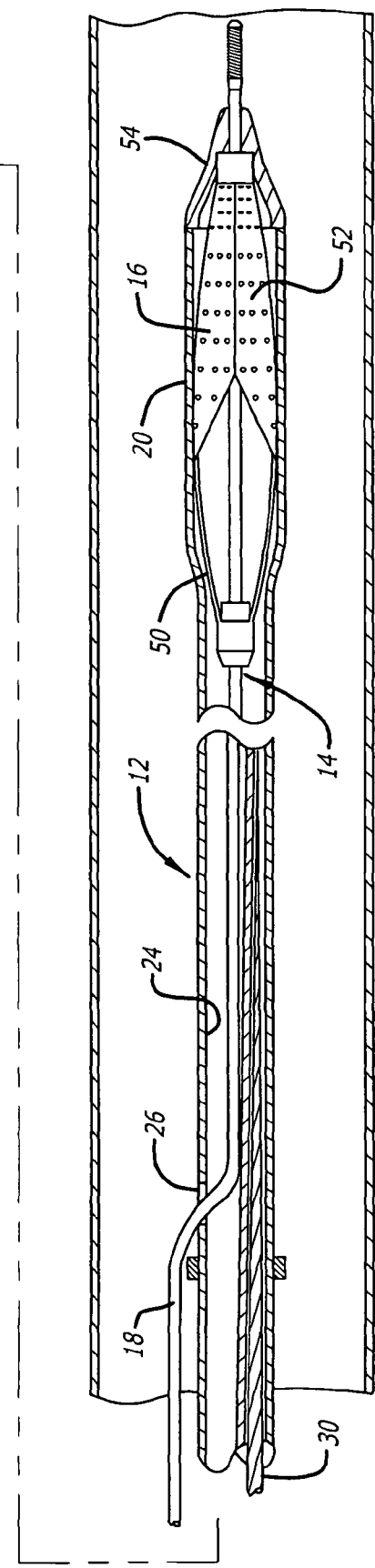
FIG. 2

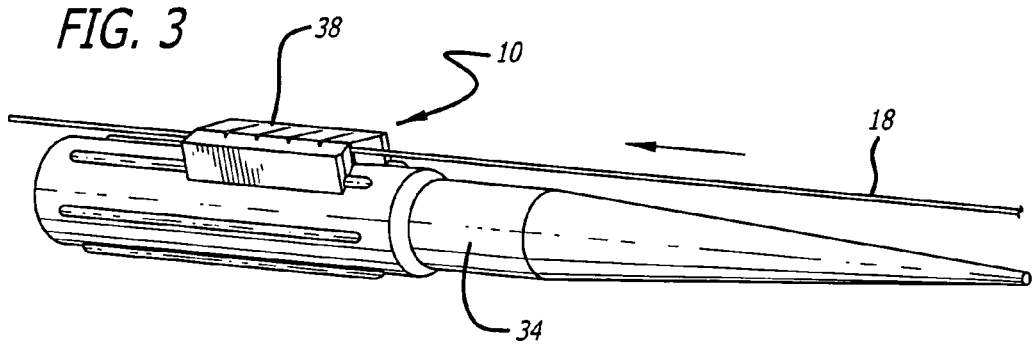
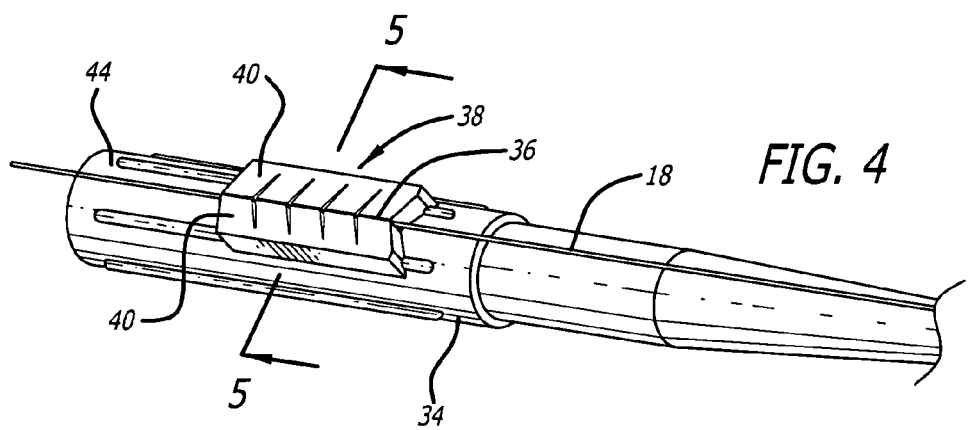
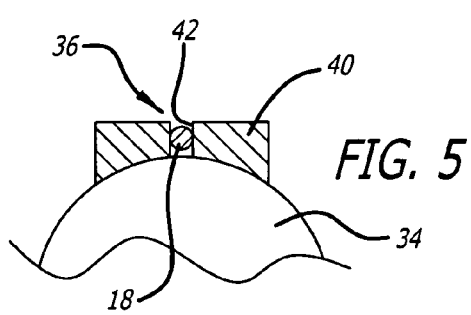
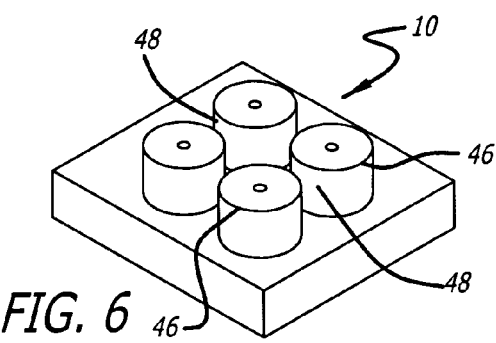
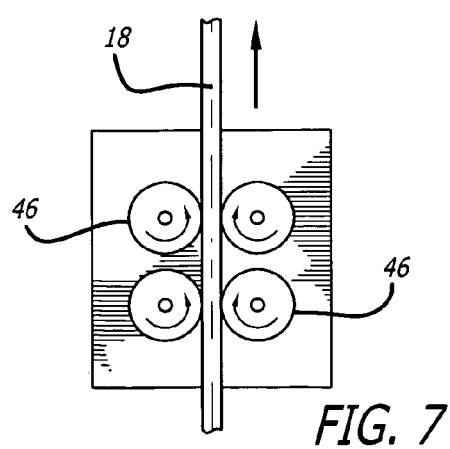

GUIDE WIRE LOCKING MECHANISM FOR RAPID EXCHANGE AND OTHER CATHETER SYSTEMS

BACKGROUND OF THE INVENTION

The present invention relates generally to catheters for use in conjunction with specialized medical devices, such as embolic filtering systems used when an interventional procedure is being performed in a stenosed or occluded region of a body vessel to capture embolic material that may be created and released into the vessel during the procedure. Additionally, the present invention can be used in conjunction with other medical delivery catheters utilized in body vessels.

Numerous procedures have been developed for treating occluded blood vessels to allow blood to flow without significant obstruction. Such procedures usually involve the percutaneous introduction of an interventional device into the lumen of the artery, usually through a catheter. One widely known and medically accepted procedure is balloon angioplasty in which an inflatable balloon is introduced within the stenosed region of the blood vessel to dilate the occluded vessel. Stents also are widely known devices which can be inserted into the patient's arterial system to provide scaffolding in the area of a stenosis in the artery. In these procedures, enhanced blood flow should resume in the dilated artery. Unfortunately, when a stenting or angioplasty procedure is performed in a highly vulnerable artery, such as the carotid artery, there is always a possibility that plaque could break away from the area of stenosis and enter the bloodstream. The deposits or plaque may also rupture and form blood clots or thrombi that can completely obstruct blood flow in the affected artery or break free and travel, emboli, to another part of the body. If either of these events occurs, the individual may suffer a myocardial infarction if the artery or arteries affected perfuse the heart or a stroke if the artery or arteries affected supply blood to the brain. If the artery or arteries affected supply blood to a limb or appendage, gangrene could possibly result. If the artery or arteries affected supply blood to the kidney or the kidneys, renal ischemia, infarction or renal failure could possibly result.

Medical devices have been developed to attempt to deal with the problem created when debris or fragments enter the circulatory system during vessel treatment. One technique which has had some success include the placement of a filter or trap downstream from the treatment site to capture embolic debris before it reaches the smaller blood vessels downstream. The placement of a filter in the patient's vasculature during treatment of the vascular lesion can reduce the presence of the embolic debris in the bloodstream. Some prior art expandable filters are attached to the distal end of a guide wire or guide wire-like member that allows the filtering device to be placed in the patient's vasculature. The guide wire allows the physician to steer the filter to a downstream location from the area of treatment. Once the guide wire is in proper position in the vasculature, the embolic filter can be deployed to capture embolic debris. These embolic filtering devices usually utilize a restraining sheath to maintain the expandable filter in its collapsed position. Once the proximal end of the restraining sheath is retracted by the physician, the expandable filter will move into its fully expanded position. The restraining sheath can then be removed from the guide wire allowing the guide wire to be used by the physician to deliver interventional devices, such as a balloon angioplasty catheter or a stent delivery catheter, into the area of treatment. After the interventional procedure is completed, a recovery sheath can be delivered over the guide wire using over-the-wire or rapid exchange techniques to collapse the expanded filter (with the trapped embolic debris) for removal from the patient's vasculature. Both the delivery sheath and recovery sheath should be relatively flexible to track over the guide wire and to avoid straightening the body vessel once in place.

While a filter can be effective in capturing embolic material, the filter still needs to be collapsed and removed from the vessel without causing any of the trapped embolic material from escaping from the filtering portion. During the recovery step, there is a possibility that trapped embolic debris can backflow through the inlet opening of the filter and enter the bloodstream as the filter is being collapsed. Additionally, as the recovery catheter and filter device are being simultaneously removed from the patient, the catheter must remain properly disposed over the filter to maintain it in the collapsed position. If the restraining sheath should somehow retract off of the expandable filter, it is possible that the filtering portion could re-deploy as the devices travel through the patient's vasculature. Such an occurrence is not desired and could cause unwanted trauma to the body vessel, release of captured emboli into the body vessel, and/or compromised filter basket integrity.

Various types of recovery catheters can be utilized to perform the recovery step. Some catheters are full-length which use a long restraining sheath that extends from the area of treatment to an area outside of the patient. These catheters, however, usually require a long length guide wire to be utilized. Moreover, when full-length sheaths are used for recovery, more time is usually needed to remove or advance the sheath along the guide wire. For this reason, recovery catheters utilizing rapid-exchange technology have been developed. A rapid-exchange recovery catheter only utilizes a short section of sheathing at its distal end to capture the deployed filter. The remaining proximal portion of recovery catheter can be made from an elongate component, such as a mandrel, a guide wire or tubing. This type of recovery catheter does not require a long length guide wire and is usually can be advanced much quicker along the guide wire than a full-length catheter. Removal of a rapid-exchange catheter is usually much faster as well.

Regardless of whether the recovery catheter is a rapid-exchange type or a full length sheath, the distal end of the recovery catheter must remain in place over the collapsed filter device to prevent backflow of captured embolic debris. Since both the recovery catheter and guide wire are usually being removed simultaneously during the recovery step, the recovery catheter cannot be retracted faster than the guide wire since such a movement could cause the recovery catheter to retract from the filter device which again can cause the problems addressed above. For this reason, it would be advantageous if the recovery catheter and guide wire could some how be locked together to permit only simultaneous movement of these components. What is needed then is a reliable recovery sheath that minimizes the risk that the restraining sheath can somehow be removed from the filtering portion during recovery. The recovery catheter should be relatively easy for a physician to use and should provide an effective means for retrieving the device without releasing any captured embolic debris into the body vessel. Moreover, it would be advantageous if the catheter can be advanced and removed from the guide wire in relatively quick fashion. The invention disclosed herein satisfies these and other needs.

SUMMARY OF THE INVENTION

The present invention provides a locking mechanism, which can be used in conjunction with a catheter used, for example, to collapse and recover an embolic filter device, mounted to a guide wire. The locking mechanism of the present invention allows the catheter to be locked to the guide wire to limit the movement of the catheter relative to the guide wire after, for example, the recovery catheter has collapsed and retrieved the filter device. In one aspect of the present invention, the locking mechanism will limit the direction of motion that the guide wire can take relative to the catheter. As such, the guide wire can move in one direction within the locking mechanism, but is prevented from moving in the opposite direction by components forming the locking mechanism. Thus, the locking mechanism allows the guide wire to move in one direction relative to the recovery catheter while preventing the guide wire from moving in the opposite direction to effectively prevent unwanted motion between the recovery catheter and guide wire.

The locking mechanism of the present invention is particularly useful when utilized in conjunction with a recovery catheter used to collapse and retrieve a filtering device attached to a guide wire. The locking mechanism will allow the recovery catheter to slide over the guide wire in one direction to allow the recovery catheter to collapse and retrieve the filtering device but will prevent the recovery catheter from moving in the opposite direction along the guide wire. This locking feature will prevent the recovery catheter from sliding away from the filter device once the filter device is collapsed and captured. In this manner, there is little chance that the filter device will be displaced from the recovery catheter as the guide wire and recovery catheter are being simultaneously removed from the patient's vasculature.

In another aspect of the present invention, a recovery catheter utilizing the features of the present invention includes a housing portion adapted to collapse and hold the filter device to allow the filter device to be removed with the recovery catheter from the patient. The housing portion can be attached to an intermediate section, formed by an elongate member, such as a mandrel or guide wire, which extends proximally from the housing portion. The proximal end of the catheter is designed to extend outside of the patient and is utilized by the physician to first move the housing portion along the guide wire to position where the housing portion is adjacent to the filter device. The proximal end of the recovery catheter includes a handle having an embodiment of the guide wire locking mechanism of the present invention attached thereto. The housing portion may include a lumen that serves as a rapid exchange port for receiving the guide wire of the embolic filtering device. The housing portion of the sheath can be made from a number of different materials and configurations to maintain the filter device in its collapsed position while the recovery catheter and filtering device are being removed from the patient's anatomy.

The housing portion has sufficient strength to impart an inward radial force that compresses the filtering device to its smaller diameter permitting the filter device to be subsequently removed from the patient. Once the filtering device is drawn into the housing portion of the catheter, it will be "encapsulated" to prevent emboli trapped in the filter basket from "back washing" into the body vessel, thus preventing the re-release of potentially damaging emboli into the patient's vasculature. The locking mechanism of the present invention prevents the guide wire and housing portion from moving relative to each other to maintain the filtering device "encapsulated" by the housing portion as the guide wire and catheter are simultaneously removed from the patient.

In another aspect of the present invention, the locking mechanism may include an opening which receives a portion of the guide wire. A motion-limiting component which allows the guide wire to move in only one direction relative to the recovery catheter is disposed along the opening. In one aspect of the present invention, the motion-limiting component can include a plurality of "teeth" aligned in a row or a pair of oppositely facing rows and adapted to contact the guide wire. The teeth can be angled back towards the proximal end of the handle to make it possible to pull the guide wire tight, since the teeth will easily move in the same direction that the guide wire is being moved. However, the teeth will prevent the guide wire from moving in the opposite direction since the teeth will "tighten" against the guide wire, preventing motion if one attempts to move the guide wire in the opposite direction. These teeth can be made from soft material that will allow them to slightly bend while still providing a contact surface with sufficient friction to hold the guide wire and prevent motion in one direction.

It is to be understood that the present invention is not limited by the embodiments described herein. Other features and advantages of the present invention will become more apparent from the following detailed description of the invention, when taken in conjunction with the accompanying exemplary drawings.

BRIEF DESCRIPTION OF THE DRAWINGS

FIG. 2 is an elevational view, partially in cross section, of the proximal and distal end of the rapid exchange recovery catheter of FIG. 1, with an embolic filtering device housed within the distal housing of the catheter and shown placed within a body vessel.

FIG. 3 is a perspective view of the proximal end of the rapid exchange recovery catheter of FIG. 1 showing a guide wire disposed within one particular embodiment of a guide wire locking mechanism made in accordance with the present invention.

FIG. 4 is another perspective view of the particular embodiment of the guide wire locking mechanism of FIG. 3.

FIG. 5 is an end view, partially in cross-section, taken along line 5-5 of FIG. 4 showing the guide wire disposed within the guide wire locking mechanism.

FIG. 6 is a perspective view of another particular embodiment of a guide wire locking mechanism which can be used with a delivery or recovery catheter.

FIG. 7 is a plan view of the particular embodiment of the guide wire locking mechanism depicted in FIG. 6.

DETAILED DESCRIPTION OF THE PREFERRED EMBODIMENTS

Figure 1:
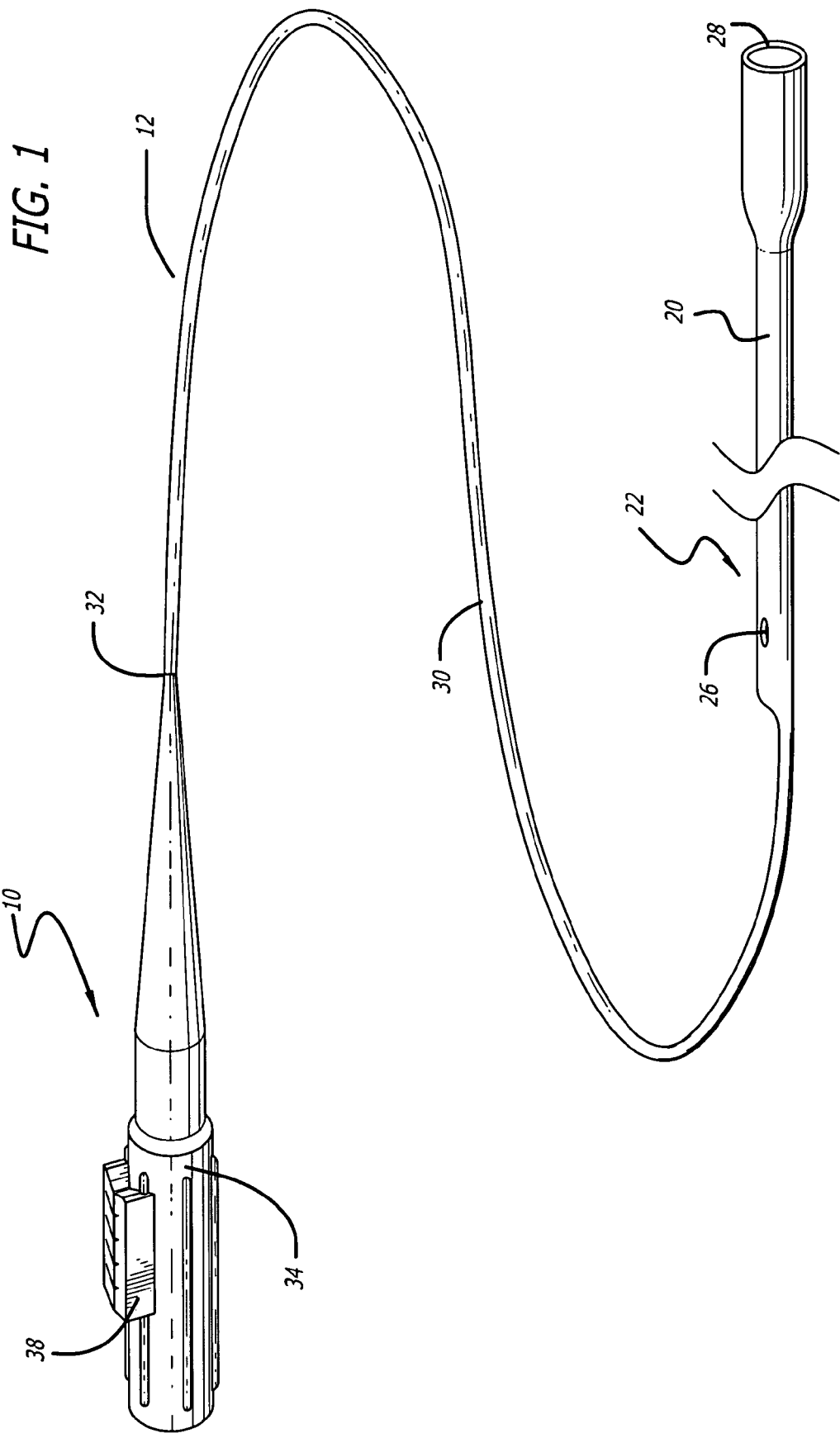
FIG. 1 is a perspective view of a rapid exchange recovery catheter with a guide wire locking mechanism made in accordance with the present invention.

Turning now to the drawings, in which like reference numerals represent like or corresponding elements in the drawings, FIGS. 1 and 2 illustrate a locking mechanism 10 used with a recovery catheter 12 which incorporate features of the present invention. This recovery catheter 12 is adapted for use with a medical device such as an expandable embolic filter device 14 designed to capture embolic debris that may be created and released into a body vessel during an interventional procedure. The recovery catheter 12 and locking mechanism 10 can be used to recover the filtering portion 16 of the embolic filter device 14 while holding the guide wire 18 in place to prevent relative movement between the recovery catheter 12 and guide wire 18 as these devices are being simultaneously retrieved from the patient.

FIGS. 1 and 2 show a particular embodiment of a recovery catheter 12 that utilizes rapid-exchange technology to allow for quick advancement along the guide wire 18. The recovery catheter includes a housing portion 20 found at the distal end 22 of the recovery catheter. This housing portion 20 is a tube-like member having a lumen 24 through which the guide wire extends. This lumen also creates a space for receiving the filtering portion 16 of the embolic filter device 14 as is shown in FIG. 2. As can be seen in FIGS. 1 and 2, this housing portion 20 can include a flared distal end which creates additional volume for receiving the filtering portion 16 of the embolic filter device 14. The housing portion 20 includes a side port 26 through which the guide wire extends along with a distal opening 28 for receiving the filtering portion 16.

The recovery catheter 12 includes an intermediate section formed by an elongate member, such as mandrel 30. The distal end of the mandrel may be secured within a lumen formed in the housing portion 20 as is shown in FIG. 2. The recovery catheter 12 has a proximal end 32 which includes a handle 34. This handle 34 can be held by the physician when advancing and positioning the recovery catheter 12 along the guide wire 18 to position the housing portion 20 over the filtering portion 16. The handle 34 has the locking mechanism 10 affixed thereto for locking the guide wire to the recovery catheter after the filtering portion 16 is collapsed and retracted within the lumen 24 of the housing portion 20. Once the guide wire is placed in engagement with the locking mechanism, as is shown in FIG. 2, the recovery catheter 12 and guide wire 18 remain locked to prevent any accidental movement between catheter and guide wire that could cause the housing portion 20 from retracting from the collapsed filtering portion 16.

Referring now to FIGS. 3-5, one particular embodiment of a locking mechanism 10 made in accordance with the present invention is shown. The locking mechanism 10 is shown including an opening 36 adapted to receive a portion of the guide wire 18. A motion-limiting component 38, which allows the guide wire 18 to move in only one direction within the locking mechanism and relative to the recovery catheter, is disposed along this opening 36. In this particular embodiment of the present invention, the motion-limiting component 38 form a number of "teeth 40" aligned in rows and adapted to make contact the guide wire. Each tooth 40 has a contact surface or face 42 adapted to make contact with the guide wire 18 as it extends within the opening 36. Each tooth 40 also can be angled back towards the proximal end 44 of the handle 34 to make it possible to pull the guide wire 18 tight, since the teeth 40 will easily move in the proximal direction allowing the guide wire 18 to be pulled back. However, the teeth 40 will prevent the guide wire 18 from moving in the opposite direction since the teeth 40 will "tighten" against the guide wire 18, preventing motion. In this manner, the rows of teeth function somewhat like a "featherboard" used in wood working in that the teeth will move and allow movement of a component in one direction while preventing movement in an opposite direction. While two rows of teeth 40 are disclosed in FIGS. 3-5, it should be appreciated that only one row could be used provided that the other row is replaced with a structure, such as an abutting surface, which cooperatively form the opening 36 of the locking mechanism 10. Also, the number, size and shape of each tooth 40 could be varied as needed, as well as the spacing between teeth. It should be appreciated that the rows of teeth are aligned such that the opening 36 is formed therebetween. In this manner, all of the contact faces 42 of the teeth should be disposed relative to each other to form an opening which is sufficiently large to receive the diameter of the particular guide wire to be used in the procedure. It should also be appreciated by those skilled in the art that the teeth can be placed relative to each other to vary the size, length and position of the guide wire opening as may be desired.

These teeth 40 can be made from a material that will allow them to bend while still providing a contact surface with sufficient friction to hold the guide wire and prevent motion in one direction. It should be appreciated that in accordance with the present embodiment, if one should attempt to move the guide wire 18 in the opposite direction of motion, the teeth 40 will not move back to their original position, but rather, will maintain tightly abutted against the guide wire 18 to prevent it from being moved in the opposite direction. For this reason, the contact surface or face 42 of each of the teeth must allow the guide wire 18 to be moved in one direction, but sufficient rough to prevent the guide wire from being accidentally moved in the opposite direction. In this manner, the teeth and their associated contact surfaces cooperate to prevent the guide wire from moving in the undesired opposite direction. It also would be possible to utilize a different material for the contact face 42 on each tooth 40, if desired, in order to obtain the desired characteristics described above. In this regard, the contact face 42 could be easily bonded or affixed to each tooth in order to achieve the necessary frictional surface needed in order for the locking mechanism to function properly. Suitable materials for the teeth and contact surface include, but are not limited to, polymeric materials, such as PEBAX, rubber, and elastomers.

Another locking mechanism made in accordance with the present invention is shown in FIGS. 6 and 7. In this particular embodiment, the motion-limiting component 38 is shown as a number of rotating wheels 46 which perform substantially the same function as the teeth 40 in the previously described embodiment. Each wheel 46 is arranged relative to each other to create a guide wire opening 36 through which the guide wire 18 can extend. Each wheel 46 has a contact surface or face 48 that makes contact with the guide wire 18. Each wheel 46 is adapted to rotate in only one direction to create a composite set of wheel that allows the guide wire to move in only one direction while preventing movement in the opposite direction. Mechanisms allowing the wheel to rotate in only one direction are well known and any one could be used to achieve one-direction rotation of each wheel 46. The direction of rotation of each wheel 46 is shown by arrows in FIG. 7. Another arrow shows the direction in which the guide wire 18 can move within the locking mechanism and relative to the catheter. Any attempt to move the guide wire in an opposite direction will be prevented by the wheels since the wheels are designed not to rotate in an opposite fashion. The contact face 48 of each wheel 46 also should provide sufficient frictional contact to hold the guide wire 18 in place and prevent it from moving in the opposite direction.

The overall length of the recovery catheter 12 should be approximately 75 to 190 centimeters. The overall length of the catheter will depend, of course, upon the type of medical component being used in accordance with the recovery catheter, along with the location of the intended area of treatment and the area of access on the patient. These dimensions can vary accordingly. The housing portion 20 should be at least about 3 centimeters in length to properly hold the filtering portion 16. It should be appreciated that the size of the housing portion 20 would vary in accordance with the size and length of the medical component it is restraining. For example, as would be shown below, different medical devices can be used in conjunction with the present invention which may have a larger or smaller overall length that would change the size needed for the housing portion 20. It should be appreciated that the lengths of the various components forming the recovery catheter can vary depending upon any given application. It should be noted that although a mandrel is shown in the disclosed embodiment to form the intermediate section, the elongate member can be any one of a number of different structures including a guide wire, tubing such as hypo-tubing, polymeric tubing and the like.

The embolic filter device 14 shown in FIG. 2 is a conventional filtering device that includes the filtering portion 16 having a plurality of self-expanding struts 50 attached to a filtering element 52. The embolic filter device 14 also includes an obturator 54 affixed to the distal end of the filtering portion 16 to prevent possible "snowplowing" of the embolic filtering device during delivery to the vasculature. This obturator can be made from a soft polymeric material, such as PEBAX 40 D.

In use, the embolic filter device 14 would be delivered within a body vessel of the patient, such as an artery. The filtering portion 16 would be placed downstream from an area of treatment where an interventional procedure is to be performed. In this manner, the area of treatment might be an atherosclerotic stenosis in which plaque has built up against the inside wall of the artery. The therapeutic interventional procedure may comprise the implantation of a stent to increase the diameter of the occluded artery and increase the blood flow therethrough. In a typical procedure, the embolic filtering device is deployed in the area of treatment to collect embolic particles created during the procedure. Interventional devices are advanced over the guide wire to the area of treatment to perform the desired procedure. After the procedure is completed, the interventional device is retracted from the patient along the guide wire. Next, the recovery catheter is placed on the guide wire and advanced to the area of treatment. Once the housing portion 20 reaches the filtering portion of the embolic filtering device, the guide wire, which extends outside of the patient, can be placed within the locking mechanism by simply inserting the guide wire into the opening 36. Thereafter, the physician can further advance the recovery catheter 12 such that the housing portion 20 contacts the struts of the embolic filtering portion causing them to collapse and be withdrawn into the lumen of the housing portion. As the distal tip of the housing portion 20 extends over the struts 50 of the filtering portion 16, forces imparted by the housing portion 20 cause the struts to move back to the collapsed position. In this fashion, the filtering portion 16 is pulled back into the housing portion and is fully encapsulating to prevent any embolic debris that which may have been collected in the filter element 52 from backflowing into the body lumen. At this point, since the guide wire is in engagement with the locking mechanism, the only direction in which the recovery catheter can continue is in a distal direction in order to fully encapsulate the filtering portion. Any attempt to pull back on the recovery catheter in a proximal direction will be prevented by the motion-limiting component 38 of the locking mechanism 10. Once the filtering portion is placed within the housing portion of the recovery catheter, the entire recovery catheter 12 and guide wire 18 with filtering portion 16 can be removed from the patient's vasculature. Since the recovery catheter cannot move back since the guide wire is in engagement with the locking mechanism, the possibility that the housing portion of the recovery catheter can somehow become retracted is greatly diminished. Accordingly, the components can be simultaneously withdrawn from the patient without the chances of the filtering portion moving out of the housing portion of the recovery catheter. It should be appreciated that the guide wire could also be placed in engagement with the locking mechanism well before the housing portion is advanced over the guide wire. In this case, since the recovery catheter can move in a distal direction along the guide wire, there should be no impediment in the physician's ability to move the recovery catheter distally along the guide wire. These particular sequences are typical of the manner in which the embodiments disclosed and described herein would functions during usage. Other methods also could be developed. This is regardless of whether the housing portion is formed as a rapid exchange-type sheath or is incorporated into a full-length sheath. Accordingly, it should be appreciated that the locking mechanism could be used with a rapid exchange type catheter or a full-length catheter.

It should be appreciated that the embodiments of the present invention are illustrated and described herein by way of example only and not by way of limitation. Also, those skilled in the art will appreciate that the present invention can be used in other body vessels, such as the coronary arteries, carotid arteries, renal arteries, saphenous veins and other peripheral arteries. Additionally, the present invention can be utilized to recover an embolic filtering device when a physician performs any one of a number of interventional procedures, such as balloon angioplasty, laser-angioplasty or atherectomy, which requires the need for a filtering device to be located downstream from the area of treatment.

It should be appreciated that the locking mechanism of the present invention can be used with a number of other different types of catheter systems besides a recovery catheter for collapsing and recovering an embolic filtering device from a patient's vasculature. The present invention can be utilized with any catheter system which requires the use of a locking mechanism to lock a guide wire to the catheter system. Additionally, while the present invention is shown in conjunction with a recovery catheter, it could also be adapted for use with delivery catheters as well. Additionally, the medical device utilized with the catheter of the present invention can be a number of other medical devices which can be implanted in a patient, besides an embolic filtering device.

Friction between the recovery catheter and medical component can be reduced by applying a coat of silicone lubricant, such as Microglide®, to the inside surface of the housing portion of the recovery catheter before the catheter is placed over the guide wire. Additionally, the elongate member, i.e. the mandrel, can be coated with a polymeric coating, or PTFE (Teflon®) in order to provide a lubricious coating which helps when advancing the device through the guide catheter (not shown).

In view of the foregoing, it is apparent that the devices of the present invention substantially enhance the safety and efficiency of recovering embolic protection devices, and other medical devices, in a patient's vasculature. Further modifications and improvements may additionally be made to the system and method disclosed herein without departing from the scope of the present invention. Accordingly, it is not intended that the invention be limited, except as by the appended claims.

What is claimed is:

1. A recovery catheter for collapsing and retrieving a filter device mounted on a distal portion of a guide wire, the recovery catheter comprising:
    a flexible housing portion adapted to collapse and maintain the filter device in a collapsed position on the guide wire, the flexible housing having a distal end and a proximal end;
    a flexible intermediate section having a distal end and a proximal end, the distal end of the intermediate section being fixedly attached to the proximal end of the housing portion; and a proximal section fixedly attached to the proximal end of the intermediate section, the proximal section having a locking mechanism which receives and engages a portion of the guide wire, the locking mechanism allowing the housing portion, intermediate portion and proximal section to slide distally along the guide wire in only one direction of motion, the locking mechanism engaging the guide wire to prevent the housing portion, intermediate section and proximal section from moving proximally along the guide wire, wherein the housing portion and intermediate section are adapted to be inserted into a body vessel and the guide wire includes a proximal portion that extends proximally from the proximal section when engaged therein.

2. The recovery catheter of claim 1, wherein:
the locking mechanism includes an opening adapted to receive a portion of the guide wire and a motion-limiting component which contacts the portion of the guide wire extending into the opening to allow the guide wire to move in only one direction within the opening.

3. The recovery catheter of claim 2, wherein:
the intermediate section is formed from an elongate member.

4. The recovery catheter of claim 3, further including:
a handle at the proximal section of the recovery catheter upon which the locking mechanism is attached.

5. The recovery catheter of claim 4, wherein:
the motion-limiting component includes a contact face which contacts the guide wire to allow only one-directional movement of the guide wire within the opening of the locking mechanism.

6. The recovery catheter of claim 5, wherein:
the motion-limiting component is a plurality of teeth aligned in a row, each tooth having a contact face which contacts the guide wire, each tooth being adapted to allow movement of the guide wire in one-direction within the opening while preventing movement in the opposite direction.

7. The recovery catheter of claim 6, wherein the motion-limiting component further includes a second row of teeth, the second row of teeth being disposed opposite the first-mentioned row of teeth, each tooth of the second row having a contact face which contacts the guide wire.

8. The recovery catheter of claim 7, wherein:
the contact faces of each row of teeth are aligned relative to each other to form the opening which receives the guide wire.

9. The recovery catheter of claim 8, wherein:
the teeth of the motion-limiting component are made from a soft polymeric material.

10. The recovery catheter of claim 9, wherein:
the teeth of the motion-limiting component are adapted to move in the one direction of motion of the guide wire within the opening of the locking mechanism.

11. The recovery catheter of claim 9, wherein:
the teeth of the motion-limiting component are adapted to move in the one direction of motion of the guide wire within the opening of the locking mechanism but not in the opposite direction when the guide wire is disposed in the opening.

12. The recovery catheter of claim 9, wherein:
the motion-limiting component includes a plurality of wheels which rotate in only one direction about an axis, the wheels being aligned relative to each other to form the opening for receiving the guide wire, the wheels permitting movement of the guide wire in only one-direction.

13. The recovery catheter of claim 9, wherein:
the motion-limiting component forms the opening for receiving the guide wire.

14. The recovery catheter of claim 9, wherein:
the teeth of the motion-limiting component are adapted to partially move in the direction of permitted travel of the guide wire within the opening of the locking mechanism.

15. The recovery catheter of claim 1, wherein the housing portion includes a lumen which houses the filter device.

16. The recovery catheter of claim 15, wherein the lumen of the housing portion includes a distal opening for receiving the filter device and a proximal open through which the guide wire extends.

17. A locking mechanism for a catheter which enables a guide wire to be locked to the catheter while permitting relative motion between the catheter and guide wire in only one direction, the locking mechanism comprising:
a motion-limiting component forming a portion of a flexible catheter and having an opening for receiving a portion of the guide wire, the motion-limiting component having a contact face adapted to contact and engage the portion of the guide wire disposed within the opening, the motion-limiting component allowing the catheter to move in a distal direction along the guide wire while preventing the catheter from moving proximally along the guide wire, the guide wire including a proximal portion that extends proximally from the motion-limiting component when engaged therein, wherein the proximal portion of the guide wire is adapted to be manually held by the user and the catheter is adapted to be manually held and moved by the user along the guide wire in the distal direction only when the guide wire is engaged with the motion-limiting component.

18. The locking mechanism of claim 17, wherein:
the motion-limiting component is a plurality of teeth aligned in a row, each tooth having a contact face which contacts the guide wire, each tooth being adapted to allow movement of the guide wire in one-direction within the opening while preventing movement in the opposite direction.

19. The locking mechanism of claim 18, wherein:
the motion-limiting component further includes a second row of teeth, the second row of teeth being disposed opposite the first-mentioned row of teeth, each tooth of the second row having a contact face which contacts the guide wire, the contact faces of each row of teeth are aligned relative to each other to form the opening which receives the guide wire.

20. The locking mechanism of claim 19 wherein:
the teeth of the motion-limiting component are made from a soft polymeric material.

21. The locking mechanism of claim 18, wherein:
the teeth of the motion-limiting component are adapted to partially move in the one direction of motion of the guide wire within the opening of the locking mechanism.

22. The locking mechanism of claim 17, wherein:
the motion-limiting component includes a plurality of wheels which rotate in only one direction about an axis, the wheels being aligned relative to each other to form the opening for receiving the guide wire, the wheels permitting movement of the guide wire in only one-direction.

23. The locking mechanism of claim 17, wherein:
the catheter is attached to the locking mechanism and the guide wire is slidably disposed with the motion-limiting component of the locking mechanism.

24. A recovery catheter for collapsing and retrieving a filter device mounted on a guide wire and located within a body vessel, the recovery catheter comprising:
- a catheter portion including a flexible housing portion and a flexible intermediate section, the catheter portion being adapted to be inserted into a body vessel, the housing portion being adapted to collapse and maintain the filter device in a collapsed position on the guide wire; and
- a handle coupled to the catheter portion, the handle including a locking mechanism which receives and engages a portion of the guide wire, the locking mechanism allowing the catheter portion and flexible housing portion to slide along the guide wire in only one direction of motion, the guide wire including a proximal portion that extends proximally from the handle when engaged with the locking mechanism, wherein the proximal portion of the guide wire is adapted to be manually held by the user and the handle portion is adapted to be manually held and moved by the user along the guide wire in the one-direction of motion when the guide wire engages the locking mechanism.

25. The recovery catheter of claim 24, wherein the locking mechanism is located on an outside surface of the handle.

26. The recovery catheter of claim 24, wherein the locking mechanism includes an opening adapted to receive a portion of the guide wire along with a motion-limiting component which contacts the portion of the guide wire extending into the opening to allow the guide wire to move in only one direction within the opening.

27. The recovery catheter of claim 26, wherein:
- the motion-limiting component includes a contact face which contacts the guide wire to allow only one-directional movement of the guide wire within the opening of the locking mechanism.

28. The recovery catheter of claim 24, wherein the housing portion includes a lumen which houses the filter device.

29. The recovery catheter of claim 28, wherein the lumen of the housing portion includes a distal opening for receiving the filter device and a proximal open through which the guide wire extends.

* * * * *